United States Patent [19]

Baudin et al.

[11] Patent Number: 5,084,440

[45] Date of Patent: Jan. 28, 1992

[54] ACETALS AND KETALS OF OXO-TETRALINS AND OXO-INDANES

[75] Inventors: Josianne Baudin, Annemasse, France; Alain-Pierre Bonenfant; Hans U. Gonzenbach, both of Geneva, Switzerland

[73] Assignee: Givaudan Corporation, Clifton, N.J.

[21] Appl. No.: 469,662

[22] Filed: Jan. 24, 1990

[30] Foreign Application Priority Data

Jan. 27, 1989 [CH] Switzerland ............................ 258/89
Nov. 30, 1989 [CH] Switzerland .......................... 4305/89

[51] Int. Cl.$^5$ .............................................. A61K 7/46
[52] U.S. Cl. ........................................ 512/12; 512/14;
568/592; 549/430; 549/369; 549/347
[58] Field of Search ............................. 512/12, 14, 17;
549/430, 369, 347; 568/592

[56] References Cited

U.S. PATENT DOCUMENTS

| | | | |
|---|---|---|---|
| 2,897,237 | 7/1959 | Carpenter et al. | 512/17 |
| 3,045,047 | 7/1962 | Davidson et al. | 512/17 |
| 3,509,215 | 4/1970 | Wood et al. | 512/17 |
| 3,636,113 | 1/1972 | Hall | 512/12 |
| 3,922,237 | 11/1975 | Schreiber et al. | 512/12 |
| 4,264,467 | 8/1981 | Schulte-Elte et al. | 549/347 |
| 4,352,748 | 10/1982 | Traas et al. | 512/17 |
| 4,493,790 | 1/1985 | Sprecker et al. | 512/17 |
| 4,614,611 | 9/1986 | Sprecker | 512/14 |
| 4,767,882 | 8/1988 | Suzukamo et al. | 512/17 |
| 4,950,369 | 8/1990 | Degner et al. | 204/78 |

FOREIGN PATENT DOCUMENTS

| | | | |
|---|---|---|---|
| 0040338 | 4/1979 | European Pat. Off. | 512/17 |
| 0035305 | 2/1981 | European Pat. Off. | 512/17 |
| 0301375 | 7/1988 | European Pat. Off. | 512/17 |
| 2427465 | 5/1976 | Fed. Rep. of Germany | 512/17 |
| 2848397 | 5/1980 | Fed. Rep. of Germany | 512/14 |
| 3502188 | 12/1988 | Fed. Rep. of Germany | 512/17 |
| 50-40761 | 4/1975 | Japan | 512/17 |
| 618344 | 7/1980 | Switzerland | 512/17 |

OTHER PUBLICATIONS

F. A. J. Meskens, Synthesis, 1981, pp. 501–522.
Beets et al., Recueil, vol. 77, pp. 854–871 (1958).

Primary Examiner—James H. Reamer
Attorney, Agent, or Firm—Robert F. Tavares; Linda A. Vag

[57] ABSTRACT

Novel odorants, namely acetals and ketals of alkyl-substituted oxo-tetralins and oxo-indanes, are described.

38 Claims, No Drawings

ACETALS AND KETALS OF OXO-TETRALINS AND OXO-INDANES

SUMMARY OF THE INVENTION

The invention concerns novel odorants, namely acetals and ketals of alkyl-substituted oxo-tetralins and oxo-indanes having the formula

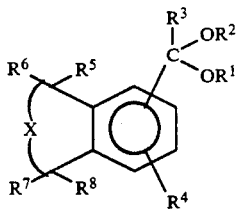

I wherein: $R^1$ and $R^2$ are selected from the group consisting of alkyl groups of one to four carbon atoms and alkenyl groups of two to four carbon atoms, or, $R^1$ in combination with $R^2$ represents an alkylene group of two to four carbon atoms wherein the substituents on said alkylene group are selected from the group consisting of
 (i) hydrogen,
 (ii) an alkyl group having one to four carbon atoms,
 (iii) an alkenyl group having two to four carbon atoms,
 (iv) an alkanol having one to four carbon atoms, and,
 (v) an alkenol having one to four carbon atoms;
$R^3$ is selected from the group consisting of hydrogen and methyl;
$R^4$ is selected from the group consisting of hydrogen, methyl, ethyl, propyl (any) and butyl (any);
$R^5$, $R^6$, $R^7$ and $R^8$ are selected from the group consisting of hydrogen, methyl, ethyl, normal-propyl and isopropyl;
X is selected from the group consisting of

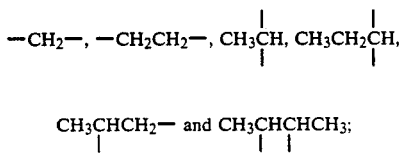

provided that
 (i) the total number of carbon atoms in $R^1$ plus $R^2$ is not greater than six;
 (ii) the total number of carbon atoms in the combination of groups $R^1$, $R^2$, $R^3$ and $R^4$ is not greater than eleven and,
 (iii) the total number of carbon atoms in the combination of groups $R^5$, $R^6$, $R^7$ and $R^8$ is not greater six.

The compounds of formula I comprise the following sub-groups:
 (a) the open-chain acetals and ketals of the oxo-tetralins;
 (b) the cyclic acetals and ketals of the oxo-tetralins;
 (c) the open-chain acetals and ketals of the oxo-indanes; and,
 (d) the cyclic acetals and ketals of the oxo-indanes.

The compounds of formula I are distinguished by very natural notes in the direction of musk, amber, woody, animalic and even fruity. These olfactive properties make the acetals and ketals particularly valuable for use in fragrance compositions. The invention, therefore also concerns fragrance compositions containing the acetals and ketals of formula I and methods for making same.

DESCRIPTION OF THE PREFERRED EMBODIMENTS

The novel acetals and ketals of fomula I may be prepared by acetalizing or ketalizing a compound of the formula

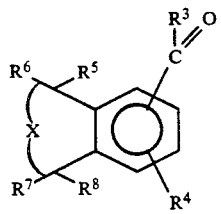

II by adapting methods known per se or trans-acetalizing or trans-ketalizing a compound of formula I or electrochemically oxidizing a compound of the formula

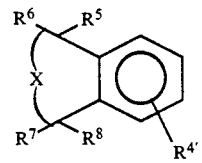

III wherein $R^{4'}$ represents methyl or ethyl. The electrochemical oxidation is carried out in the presence of an alcohol $R^{2'}OH$, namely a $C_{1-3}$-alkanol, and a conducting salt. General methods for the manufacture of acetals and ketals is known. (See e.g. A. J. Meskens, Synthesis (1981), 501 et seq. or DT-OS 2848397.) Methods which may be used for the manufacture of a compound of formula I are as follows:
 (A) Compound II + orthoformic acid ester;
 (B) Compound II + alcohol;
 (C) Compound II + diol (suitable for the cyclene);
 (D) Transacetalization or transketalization of compound I: and.
 (E) Electrochemical.

The following illustrates the adaption of these methods to the present invention:

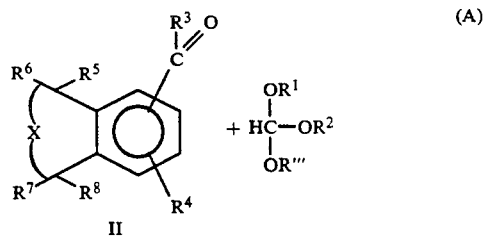

(A)

wherein $R^1$ and $R^2$ are $C_{1-4}$-alkyl and $R'''$ is normally the same as $R^1$ or $R^2$.

Parameters:
Temperature range: About 10° C. to about 110° C. especially about 20° C. to about 40° C.:
Additional solvent (optional): Alkanols, hexane, cyclohexane, etc.;

Catalysts: Acids, e.g. HCl, p-toluenesulphonic acid, $Al_2O_3.4SiO_2.nH_2O$. acidic salts, e.g. $KHSO_4$, acidic ion exchanger;

Isolation of the compound: Distillation under reduced pressure, column chromatography.

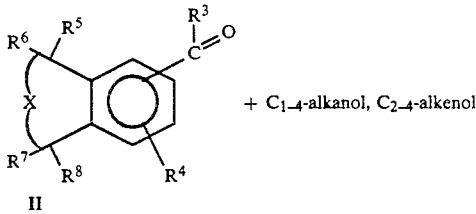

(B)

Parameters:

Temperature range: About 10° C. to about 100° C.:

Additional solvent: $CH_2Cl_2$. $C_6H_6$, toluene, etc.;

Catalysts: (Lewis) acids, e.g. HCl, $H_2HNO_3$, toluenesulphonic acid, $BF_3$, sulphosalicylic acid, acidic salts, e.g. $KHSO_4$, ion-exchanger;

Isolation of the compound I: Distillation under reduced pressure, column chromatography.

(C)

Reaction of 11 with a corresponding, optionally substituted diol, e.g. ethanediol, 1,2-propanediol, 1,3-propanediol, 1,2-butanediol, 2,3-butanediol, 1,3-butanediol, 2-butene-1,4-diol, 2-methyl-1,4-butane-diol, etc. This method can, of course, also be carried out using polyols, e.g. glycerol, 1,2,3-pentanetriol, 1,2,3,4-butanetetraol, 1,2,4-butanetriol and isomers thereof, etc.

Parameters

Additional solvent (optional): Ether, (chlorinated) hydrocarbons;

Catalysts: Acids, including Lewis acids, acidic salts, etc.;

Temperature range: About 30° C. to about 150° C.;

Isolation: Distillation, crystallization.

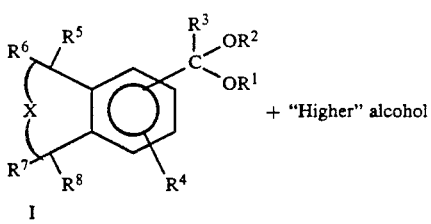

(D)

The transacetalization or transketalization of I. particularly wherein the $R^1$ or $R^2$ of a low-boiling alcohol is replaced by the substitutent of a higher-boiling alcohol. The higher alcohol may also be a diol. The equilibrium also depends on the amount of the alcohol which is used.

Parameters:

Temperature range: About 65° C. to 85° C.;

Additional solvent: Toluene, etc.;

Isolation of the compound 1: E.g. by distillation.

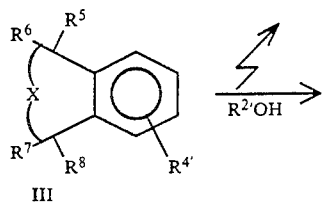

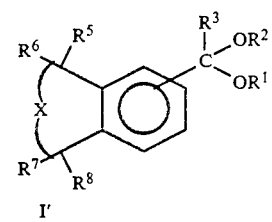

wherein $R^{4'}$is $CH_3$ or $C_2H_5$ and $R^{2'}pH$ is $C_{1-3}$-alkanol or $C_{1-3}$-alkanediol. The substituents $R^1$ and $R^2$ correspond to the alcohol $R^{2'}OH$ which is used.

The electrochemical method is conveniently carried out as described in detail e.g. in DT-OS 2848397. Convenient parameters are accordingly:

Cell: Divided or undivided; Electrolyte: Solution of III in the alcohol used, which contains the conducting salt;

Conducting salt: Conducting salts which are usual in electrochemistry. Well-suited are e.g. salts which are soluble in the solution to be electrolyzed and which are largely stable under the conditions of the experiment. Examples of especially suitable conducting salts are fluorides such as KF, tetrafluoroborates such as $Et_4NBF_4$, perchlorates such as $Et_4NClO_4$, sulphates such as $Et_4NSO_4Et$, alcoholates such as $NaOCH_3$ and hydroxides such as KOH;

Anode material: Examples of suitable anode materials are graphite, graphite-filled plastic materials, noble metals such as platinum and gold as well as noble metal-coated titanium electrodes;

Cathode material: For example, graphite, iron, steel, lead or noble metal electrodes;

Current density: For example, 1-5 $A/dm^2$;

Temperature: E.g. temperatures between 0° and about 60° C.;

Work-up: The electrolysis products are generally worked-up by distillation. Excess alcohol and starting material which may still be present are separated from the acetals by distillation and can be recovered by electrolysis.

The acetals and ketals of the oxo-tetralins and oxo-indanes of formula I are distinguished by very natural notes in the direction of musk, amber, woody, animalic and even fruity. The odor characteristics found for the acetals and ketals may be distinguised as follows:

Acetals:

simple. open-chain: musk, woody, fruity;

cyclic: musk;

substituted: complex aspects, olfactory strength: woody/musk/fruity/amber/animalic.

Ketals:

simple, open-chain: musk, woody, stronger fruity, less campheraceous than the corresponding acetals;

cyclic: strongly woody;

substituted: complex aspects, olfactory strength: woody/musk/fruity/amber/animalic.

A number of examples are provided below along with tables of compounds and their odor values. (See Tables I and II.) For economic reasons acetals and ketals of the oxo-tetralins are preferred. Especially preferred compounds of formula I are:

2,4-dimethyl-2-(1,1,4,4-tetramethyl-tetralin-6-yl)1.3-dioxolane,
2-methyl-4-ethyl-2-(1,1,4,4-tetramethyl-tetralin-6-yl)-1,3-dioxolane.
7-(formyl diethyl acetal)-1,1,2,4,4-pentamethyl-tetralin,
2,4-dimethyl-2-(1,1,4,4-tetramethyl-tetralin-6-yl)1.3-dioxane,
6-(acetyl diethyl ketal)-1,1,2,4,4,7-hexamethyl-tetralin,
2,4-dimethyl-2-(1,1,2,4,4,7 hexamethyl-tetralin-6-yl)1,3-dioxolane.

Compared with the basic carbonyl compounds, the acetals and ketals of formula I are generally found to be stronger, more woody, more animalic and more substantive. An important technical advantage in the use of a compound I results from the fact that some of them, when blended with the basic carbonyl compounds give liquid musky mixtures. It is thus possible by means of the novel compounds I and known musk substances, especially the corresponding "basic" substances, to manufacture by the accurate apportioning of amounts, quasi enriched sophisticated and esthetized musk substances of variable intensity and, in particular, also of variable odorous nuance. Such mixtures, i.e. aldehydes or ketones of the formula II and the corresponding acetals or ketals of formula I, are, by virtue of their pronounced substantivity and tenacity, also especially suitable for the perfuming of laundry or of fabric conditioners. (See in this respect Table III.)

The optimal ratio of compound I/"basic substance" follows in each case from the results of washing tests and of the solubility of the basic substance of the compound I. It lies, for example. between about 1:10 to 1:1. but more extreme values are also possible.

The novel acetals and ketals combine with numerous known odorant ingredients of natural or synthetic origin, whereby the range of the natural raw substances can embrace not only readily-volatile, but also moderately-volatile and slightly-volatile components and that of the synthetics can embrace representatives from practically all classes of substances, as will be evident from the following compilation:

Natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil,
alcohols, such as farnesol, geraniol, linalool, nerol, phenylethyl alcohol, rhodinol, cinnamic alcohol,
2-methyl-3,4-methylenedioxyhydrocinnamic aldehyde, α-hexyl-cinnamaldehyde, hydroxycitronellal, Lilial ® (Givaudan, p-tert.butyl-α-methyl-dihydrocinnamaldehyde), methylnonylacetaldehyde,
ketones, such as allylionone, α-ionone, β-ionone, isoraldein (isomethyl-α-ionone), methylionone,
esters, such as allyl phenoxyacetate, benzyl salicylate, cinnamyl propionate, citronellyl acetate, citronellyl ethoxolate (citronellyl.O-CO-CO.OC$_2$H$_5$). decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc.
lactones, such as y-undecalaotone.
various components often used in perfumery, such as musk ketone, indole. p-menthane-8-thiol-3-one, methyleugenol.

The acetals and ketals can be used in wide limits which can range in compositions, for example, from about 0.1 (detergents) - about 20% (alcoholic solutions), without these values being, however, limiting values, as the experienced perfumer can also achieve effects with even lower concentrations or can synthesize novel complexes with even higher amounts. The preferred concentrations range between about 1 and about 10%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, fabric conditioners, tobacco, etc.).

The acetals and ketals can accordingly be used in the manufacture of compositions and - as the above compilation shows - using a wide range of known odorants or odorant mixtures. The manufacture of the compositions is carried out in the usual manner, i.e. by mixing, as described below. In the manufacture of such compositions the known odorants referred to above can be used according to methods known to the perfumer such as e.g. from W. A. Poucher, Perfumes, Cosmetics and Soaps 2,7th Edition, Chapman and Hall, London, 1974.

ILLUSTRATION OF THE PREFERRED EMBODIMENTS

General Methodoloqy

Method A

Acetyl chloride (0.02 mol) is added dropwise within approximately 5 minutes to a mixture of the orthoformic ester (ethyl or methyl ester: 0.763 mol). 0.6 mol of ethanol or methanol and 0.28 mol of aldehyde or ketone. The reaction is slightly exothermic, with the temperature rising from about 20° C to about 40° C. The resulting mixture is stirred at room temperature for 2 hours and thereupon made alkaline to a pH of 7.5 to 8 by the addition of a 10% solution of potassium hydroxide in ethanol. After filtration, removal of the orthoformate and of the alcohol under reduced pressure, the pure acetal, for example the diethyl acetal or dimethyl acetal, is obtained by distillation.

Method B

Acetyl chloride (1.5 mmol) is added dropwise within 5 minutes to a mixture of 0.075 mol of propanol and 0.022 mol of aldehyde. The reaction mixture is heated to 65° C. and stirred at this temperature for 3 hours. After cooling to room temperature the reaction mixture is neutralized by the addition of a 10% solution of potassium hydroxide in ethanol. The reaction mixture is filtered and the filtrate is evaporated, whereby the crude acetal separates. This is purified by chromatography on silica gel using isopropyl ether/hexane in the ratio of 1:20 as the eluent.

Method C

Aldehyde or ketone (0.1 mol), 0.2 mol of diol (for example ethylene glycol or propylene glycol), 200 ml of toluene and 0.15 g of p-toluenesulphonic acid monohydrate are stirred and heated. The water which is formed during the reaction is distilled off azeotropically within 24 hours. The reaction mixture is brought to a pH value of 7.5 to 8 by the addition of a 10% solution of potassium hydroxide in ethanol. Thereupon, the mixture is filtered. After evaporation of the solvent the crude acetal is purified by distillation or recrystallization.

2,4-Dimethyl-2-[1,1,2,4,4,7-hexamethyl-tetralin-6-yl]-1.3-dioxolane

The same method may be used to prepare 2,4-dimethyl 2 [1,1,2,4,4,7-hexamethyl-tetralin-6-yl]-1,3-dioxolane starting from 6-acetyl-1,1,2,4,4,7-hexamethyl-tetralin and propylene glycol. The boiling point is 109° C. at 0,2 mmMg; nD$^{20}$=1.5182. The odour is musky, green, soft, powdery.

Method D (a) p-Toluenesulphonic acid (0.1 g) is added to a mixture of 0.066 mol of formyl acetal, e.g. 6-formyl-1,1,3,4,4-pentamethyltetralin diethyl acetal, 0.066 mol of allyl alcohol and 50 ml of toluene. The resulting mixture is stirred at 85° C. to 90° C. for 4 hours. The ethanol which is formed in the reaction is removed by distillation. Thereupon, the mixture is neutralized by the addition of 10% potassium hydroxide in ethanol, filtered and evaporated, whereby the acetal formed, for example allyl ethyl acetal, is obtained. The isolation is carried out by preparative gas chromatography.

(b) Acetyl chloride (0.1 g) is added dropwise within 5 minutes to a mixture of 0.35 mol of ethyl formate, 0.31 mol of ethanol and 0.13 mol of ketone. The reaction is slightly exothermic, resulting in a temperature increase from 20° C. to 28° C. The resulting mixture is stirred at room temperature for 2 hours. The excess orthoformate is removed by distillation in a vacuum at, for example, 50 mm Hg. The reaction mixture is cooled and 50 ml of toluene and 0.20 mol of propylene glycol are added as well as a further 1.5 mmol of p-toluenesulphonic acid. The resulting mixture is stirred at 85° C. to 90° C. for 2½ hours. The ethanol which is formed is removed by distillation. The mixture is neutralized by the addition of 10% potassium hydroxide in ethanol, filtered and the filtrate is evaporated, whereby there separates the crude acetal which can be purified by distillation.

Example 1.A 7-(Formyl diethyl acetal)-1,1,2,4,4-pentamethyl-tetralin

Acetyl chloride (0.02 mol, 1.65 g) is added dropwise at room 0 temperature within 1 minute to a stirred mixture of 113 g (0.76 mol) of ethyl orthoformate, 35 ml of ethanol and 64.3 g (0.28 mol) of 7-formyl-1,1,2,4,4-pentamethyl-tetralin. The reaction is slightly exothermic, which results in a temperature increase from 20° C. to 38° C. The resulting mixture is stirred at room temperature for 2 hours, after which time it is adjusted to a pH of 7.5 to 8 by the addition of a 10% solution of potassium hydroxide in ethanol. After filtration and removal of the excess ethanol and of the ethyl orthoformate by distillation the residual liquid is distilled in a vacuum, whereby there separates mainly 69 g of 7-(formyl diethyl acetal)-1,1,2,4,4-pentamethyl-tetralin as a colourless solution. 112° C./0.25 mmHg; n$^{20}$$_D$ 1 5015. The odour is slightly musk-like.

Example 1.B 7-(Formyl dipropyl acetal)-1,1,2,4,4-pentamethyl-tetralin

Acetyl chloride (0.25 g) is added dropwise at room temperature to a mixture of 10 g (0.04 mol) of 7-formyl-1,1,2,4,4-pentamethyl-tetralin and 10 g (0.17 mol) of n-propanol. The reaction mixture is heated to 65° C and stirred at this temperature for 2 hours. After cooling to room temperature the reaction mixture is neutralized by the addition of 10% potassium hydroxide in ethanol. The mixture is filtered and the filtrate is evaporated, whereby there separates crude 7-(formyl dipropyl acetal)-1,1,2,4,4-pentamethyl-tetralin which is purified by chromatography on silica gel. Isopropyl ether/hexane in the ratio of 1:20 is used as the eluent. The acetal is a colourless liquid; n$_D$$^{20}$=1.4980. The odour is distinctly musk-like.

Example 1.C 2,4-Dimethyl-2-(1,1,4,4-tetramethyl-tetralin-6-Yl)-1,3-dioxolane p-Toluenesulphonic acid monohydrate (2 g) is added to a suspension of 120 g (0.5 mol) of 6-acetyl-1,1,4,4-tetra-methyl-tetralin, 120 g (1.6 mol) of propylene glycol and 600 ml of toluene. The mixture is heated to 110° C. The reaction water is removed azeotropically within 5 hours. After cooling to room temperature the mixture is adjusted to pH 7.5 to 8 by the addition of 10% potassium hydroxide in ethanol. Thereupon, the mixture is filtered. The solvent is evaporated and the residual liquid is distilled under a vacuum, whereby there separate as the main product 123 g of 2.4-dimethyl-2-(1,1,4,4-tetramethyl-tetralin-6-yl)-1,3-dioxolane as a mixture of the boiling point is 112° C. at 0.5 mmHg; nD$^{20}$=1.5130. The product has a strong woody, animalic odour.

Example 1.D 2,4-Dimethyl-2-(1,1,4,4-tetramethyl-tetralin-6-yl)-1,3-dioxolane Acetyl chloride (0.15 g) is added dropwise at room temperature to a mixture of 52.5 g (0.35 mol) of ethyl orthoformate, 30 g (0.13 mol) of 6-acetyl-1,1,4,4-tetramethyl-tetralin and 18 ml of ethanol. The reaction is slightly exothermic, which results in a temperature increase from 20° C. to 28° C. The mixture is stirred at this temperature for 2 hours. The excess ethyl orthoformate and ethanol are removed by vacuum distillation (120° C./ 100 mm Hg). After this time the reaction mixture is cooled and 50 ml of toluene, 22.5 g (0.29 mol) of propylene glycol and 0.3 g of p-toluenesulphonic acid are added rapidly. The mixture is stirred at 85° C. to 90° C. for 2 1/2 hours. The ethanol which is formed is removed by distillation. Thereupon, the residual mixture is neutralized by the addition of a 10% solution of potassium hydroxide in ethanol, filtered and the filtrate is evaporated. Crude 2-dimethyl-2-(1,1,4,4-tetramethyl-tetralin-6-yl)-1,3-dioxolane is obtained. The product is purified by vacuum distillation and there are obtained 23.7 g of pure product. The boiling point of the pure product is 112° C. at 0.45 mmHg.

Example 1.E 7-(Formyl-diethyl acetal)-1,1,2,4,4-pentamethyl-tetralin 1.1,2,4,4,7-Hexamethyl-tetralin (200 g) dissolved in 500 g of cyclohexane (anhydrous) is placed in a 3 1 four-necked vessel having heating, a tap in the bottom and a reflux condenser and 1 kg of ethanol (anhydrous) containing 14 g of sulphuric acid (98%) is added while stirring. This mixture is circulated by means of a pump (10 l/min) through the electrolysis cell (filter press type having graphite anodes and Inox cathodes 6 mm apart, effective surface: 220 cm²) (potential difference 35-42 volt at 3.5-4 ampere, duration 38 hours, reservoir temperature 25-30° C.). A GC analysis indicates a content of the desired compound, namely 7-(formyl-diethyl acetal)-1,1,2,4,4-pentamethyl-tetralin, of 77%. After the addition of 18.5 g of sodium carbonate the mixture is evaporated (40° C. 20 mmHg). The 285 g remaining behind are washed with 300 g of sodium chloride solution (10%) and distilled over a Vigreux column (130° C. 3 mmHg). Yield: 224 g. 87%, purity 83% (GC). main impurity: 1,1,2,4.4-pentamethyl-7-formyl-tetralin (GC 11%).

Further compounds are listed in Tables I and II.

TABLE I

| Starting material | R¹ | R² | Method | B.p. °C. (mmHg) | M.p. °C. | $n_D^{20}$ | Odour |
|---|---|---|---|---|---|---|---|
| a) Ketals (open-chain, R³ of formula I = CH₃) | | | | | | | |
| 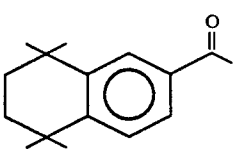 | CH₃ C₂H₅ | CH₃ C₂H₅ | A A | 93(0.1) | 44.5-46 | 1.4985 | Woody, amber Slightly woody |
| 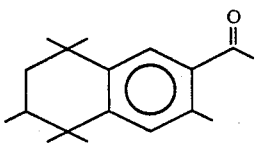 | CH₃ C₂H₅ | CH₃ C₂H₅ | A A | | 80-81.5 85-87 | | Musk, amber animalic Musk |
| 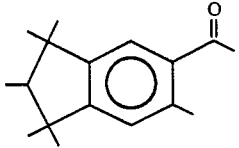 | C₂H₅ | C₂H₅ | A | | 62-63 | | Musk, woody |
| 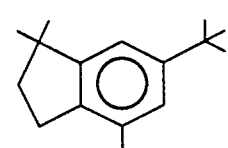 | C₂H₅ | C₂H₅ | A | 94(0.2) | | 1.4945 | Musk, animalic |
| b) Acetals (open-chain, R³ of formula I = H) | | | | | | | |
| 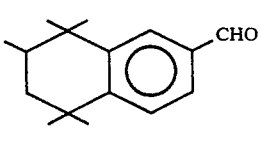 | CH₃ C₂H₅ n-C₃H₇ Allyl | CH₃ C₂H₅ n-C₃H₇ Allyl | A A B D(a) | 103(0.1) 112(0.25) | | 1.5120 1.5015 | Slightly after musk, flowery Slightly after musk, flowery After musk After musk |
| 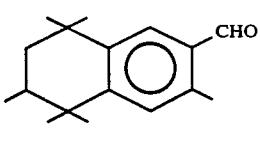 | CH₃ C₂H₅ | CH₃ C₂H₅ | A A | 108(0.1) | 50-51 | 1.5030 | After musk After musk, powdery |
| 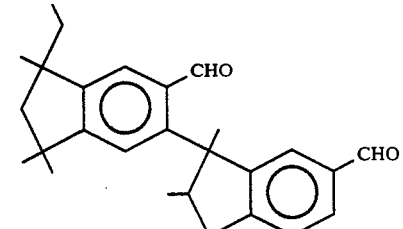 | CH₃ C₂H₅ | CH₃ C₂H₅ | A A | 146(9.5) 98(0.1) | | 1.5045 1.4950 | After musk, delicate, flowery Slightly after musk |

TABLE I-continued

| Starting material | $R^1$ | $R^2$ | Method | B.p. °C. (mmHg) | M.p. °C. | $n_D^{20}$ | Odour |
|---|---|---|---|---|---|---|---|
|  | $C_2H_5$ | $C_2H_5$ | A | 145(0.05) | | | After honey, green, flowery |

TABLE II a) Ketals (cyclic, $R^3$ of formula I = $CH^3$)

| Starting materials | $R^1 + R^2$ | Method | B.p. °C. (mmHg) | M.p. °C. | $n_D^{20}$ | Odor |
|---|---|---|---|---|---|---|
| | —CH₂CH₂— | C | | 77 | | Woody, after musk |
| | —CH₂CHCH₂OH | C | 180(0.04) | | 1.5265 | Woody, animalic |
| | —CH₂—CHCH₃ | C, E | 112(0.45) | | 1.5130 | Woody, animalic |
| | —CH₂CH₂— | C | | 111–112 | | After musk, animalic |
| | —CH₂CH₂— | C | | 112 | | Slightly after musk |
| | —CH₂CH₂— | C | | 119–120 | | After musk, tonka |
| | CH₃CHCH₂— | C | 109(0.2) | | 1.5182 | After musk, green, powdery, sweet |
| | —CH₂CH₂— | C | | 110–111 | | Slightly after musk |
| | —CH₂CH₂— | C | | 108–110 | | After musk, animalic |
| | —CH₂CH₂— | C | | 71–72 | | Woody, after musk |
| | CH₃CHCH₂— | C | 109(0.5) | | 1.5065 | Woody, animalic |

TABLE II-continued

| a) Ketals (cyclic, $R^3$ of formula I = $CH^3$) | | | | | | |
|---|---|---|---|---|---|---|
| Starting materials | $R^1 + R^2$ | Method | B.p. °C. (mmHg) | M.p. °C. | $n_D^{20}$ | Odor |
| 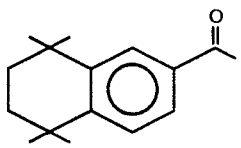 | —CH$_2$CHCH$_2$CH$_3$ | C | 109(0.5) | | | Woody, amber, animalic, tobacco |
| 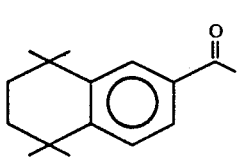 | CH$_3$CHCHCH$_3$ | C | 111(0.3) | | | Woody, amber, after musk |
| | —CH$_2$CH$_2$CH$_2$— | C | 94(0.15) | | | Slightly woody, slightly fatty |
| | —CH$_2$CH$_2$CHCH$_3$ | C | | 90–92 | | After musk, amber, woody, animalic |
| 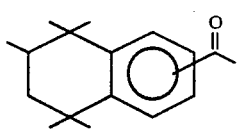 | —CH$_2$CHCH$_3$ | C | 100(0.08) | | | Woody, animalic |
| 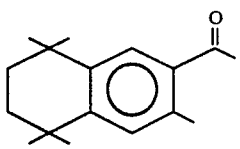 | —CH$_2$CHCH$_3$ | C | 122(0.9) | | | Slightly after musk |
| 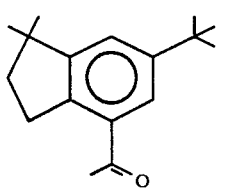 | —CH$_2$CH(OH)CH$_2$— and —CH$_2$CHCH$_2$OH | C | 140(0.65) | | | Slightly after musk, woody |
| 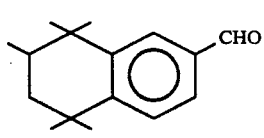 | —CH$_2$CH$_2$— | C | | 73–74 | | After musk, fruity |
| | —CH$_2$CHCH$_3$ | C | | 70–73 | | After musk, camphor |
| | —CH$_2$CH$_2$=CH$_2$CH$_2$— | C | | 75–76 | | Slightly after musk, green |
| 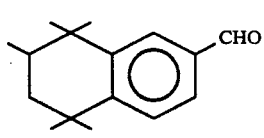 | —CH$_2$CH$_2$— | C | | 66–67 | | Slightly after musk, fatty |
| 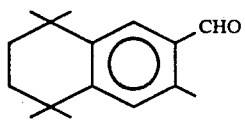 | —CH$_2$CH$_2$— | C | | 72–73 | | Slightly after musk |

TABLE II-continued a) Ketals (cyclic, $R^3$ of formula I = $CH^3$)

| Starting materials | $R^1 + R^2$ | Method | B.p. °C. (mmHg) | M.p. °C. | $n_D^{20}$ | Odor |
|---|---|---|---|---|---|---|
|  | —CH$_2$CH$_2$— | C | 110(0.18) | 50-58 | | After musk, green, musty |

| Odorant composition | Parts by weight |
|---|---|
| Bergamot essence | 250.00 |
| Lemon essence | 150.00 |
| Lavandin essence | 100.00 |
| Cetone alpha (α-isomethylionone) | 50.00 |
| Methyl dihydrojasmonate | 50.00 |
| Sandalore ® (Givaudan, 5-(2,2,3-trimethylcyclopent-3-en-1-yl)3-methylpentan-2-ol | 20.00 |
| Fixolide ® (Givaudan, 7-acetyl-1,1,3,4,4,6-hexamethyl-tetralin) | 40.00 |
| Coumarin cryst. | 20.00 |
| Nutmeg essence | 20.00 |
| Clove essence | 20.00 |
| Estragon essence | 5.00 |
| Allylamyl glycolate | 2.00 |
| Methyl 2,4-dihydroxy-3,6-dimethylbenzoate | 5.00 |
| Geranylacetate pure | 50.00 |
| Benzylacetate extra | 40.00 |
| Peche Pur (gamma-undecalactone) | 2.00 |
| Isoeugenol | 5.00 |
| Methyl anthranilate extra | 1.00 |
| Basil essence | 10.00 |
| Carbiol | 160.00 |
| | 1000.00 |

The substitution of 70 parts of 2,4-dimethyl-2-(1,1,4,4-tetramethyl-tetralin-6-yl) -1,3-dioxolane for 70 parts of carbitol confers to the composition an elegant woody note accompanied by a warm amber-like undertone. At the same time the citrus notes are underlined in an agreeable manner. The composition receives much more freshness and volume.

Comparative laundry test:

For this purpose, a conventional laundry conditioner, i.e. a laundry softener, e.g. based on the usual cation active and pseudo cation active substances, e.g. of the quaternary ammonium type, was perfumed with 0.3% (w/w) of an odorant mixture (see Table III) in the usual manner and, after the washing operation (60° C.), was added in an amount of a few g/l, e.g. ca. 3-6 g/l of water, in the specific case of 4,5 g/l for the last rinsing.

The odorant compositions were compared with an odorant mixture of 1,3,4,6,7,8-hexahydro-4,6,6,7,8 8-hexamethyl-cyclopenta-Y-2-benzopyran (Galaxo 1,1,2,4,4,7-hexamethyl-6-acetyl-1,2,3,4-tetrahydronaphthalene (Fixolide ® Giaudan) as the standard.

TABLE III

Comparative laundry test
(conventional fabric conditioner perfumed with 0.3% of odorant mixture)

| Ref | Musk/acetal or ketal % w/w (all liquid) | Evaluation Wet laundry | Dry laundry |
|---|---|---|---|
| A | GALAXOLIDE/FIXOLIDE [standard] 50:50 | relatively little intensity; musk note hardly appears | rather unpleasant; scarcely musk, fatty |
| B | 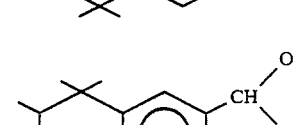 GALAXOLIDE/ 50:50 | stronger than all others, accentuated animalic woody note and costus aspect | stronger than all others, harmonic accord with animalic and patchouli notes |
| C | 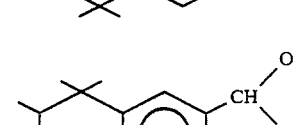 FIXOLIDE/ 50:50 | musk note of average strength + earthy aspects | agreeable musk note with non-woody aspect |

TABLE III-continued

Comparative laundry test
(conventional fabric conditioner perfumed with 0.3% of odorant mixture)

| Ref | Musk/acetal or ketal % w/w (all liquid) | Evaluation Wet laundry | Dry laundry |
|---|---|---|---|
| D | FIXOLIDE/ 55:45 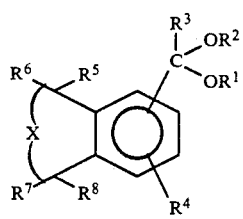 | | |
| E | FIXOLIDE/ 45:55 | + vanilla and nitromusk aspects | "clean" musk note with good persistence |

We claim:
1. A compound of the formula

   I wherein:
R$^1$ and R$^2$ are selected from the group consisting of alkyl groups of one to four carbon atoms and alkenyl groups of two to four carbon atoms, or R$^1$ in combination with R$^2$ represents an alkylene group of two to four carbon atoms wherein the substituents on said alkylene group are selected from the group consisting of
(i) hydrogen,
(ii) an alkyl group having one to four carbon atoms,
(iii) an alkenyl group having two to four carbon atoms.
(iv) an alkanol having one to four carbon atoms, and,
(v) an alkenol having one to four carbon atoms;
R$^3$ is selected from the group consisting of hydrogen and methyl;
R$^4$ is selected from the group consisting of hydrogen, methyl, ethyl, propyl and butyl;
R$^5$, R$^6$, R$^7$ and R$^8$ are selected from the group consisting of hydrogen, methyl, ethyl, normal-propyl and iso-propyl;
X is selected from the group consisting of

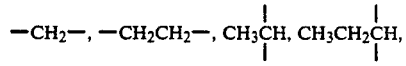

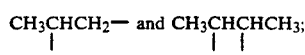

provided that
(i) the total number of carbon atoms in R$^1$ plus R$^2$ is not greater than six;

(ii) the total number of carbon atoms in the combination of groups R$^1$, R$^2$, R$^3$ and R$^4$ is not greater than eleven, and,
(iii) the total number of carbon atoms in the combination of groups R$^5$, R$^6$, R$^7$ and R$^8$ is not greater six.

2. A compound according to claim 1 wherein R$^1$ and R$^2$ are selected from the group consisting of alkyl groups of one to four carbon atoms and alkenyl groups of two to four carbon atoms and X is $$-CH_2CH_2-,\ \underset{|}{CH_3CHCH_2}-\ \text{or}\ \underset{|\ \ \ |}{CH_3CHCHCH_3}.$$

3. A compound according to claim 1 wherein R$^1$ in combination with R$^2$ represents an alkylene group of two to four carbon atoms wherein the substituents on said alkylene group are selected from the group consisting of
(i) hydrogen,
(ii) an alkyl group having one to four carbon atoms,
(iii) an alkenyl group having two to four carbon atoms,
(iv) an alkanol having one to four carbon atom, and,
(v) an alkenol having one to four carbon atoms; and X is $$-CH_2CH_2-,\ \underset{|}{CH_3CHCH_2}-\ \text{or}\ \underset{|\ \ \ |}{CH_3CHCHCH_3}.$$

4. A compound according to claim 1 wherein R$^1$ and R$^2$ are selected from the group consisting of alkyl groups of one to four carbon atoms and alkenyl groups of two to four carbon atoms and X is

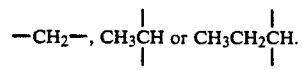

5. A compound according to claim 1 wherein R$^1$ in combination with R$^2$ represents an alkylene group of two to four carbon atoms wherein the substituents on said alkylene group are selected from the group consisting of
(i) hydrogen,
(ii) an alkyl group having one to four carbon atoms, (iii) an alkenyl group having two to four carbon atoms,
(iv) an alkanol having one to four carbon atom, and,
(v) an alkenol having one to four carbon atoms; and X is

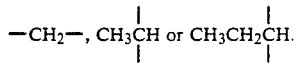

6. A compound according to claim 1 having the structure

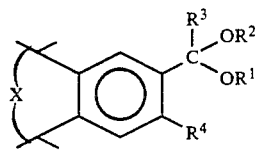

7. A compound according to claim 6 wherein $R^4$ is hydrogen or methyl and X is

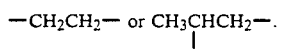

8. A compound according to claim 6 wherein $R^4$ is hydrogen or methyl and X is

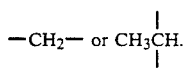

9. A compound according to claim 7 wherein $R^1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

10. A compound according to claim 8 wherein $R_1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

11. The compound according to claim 9 which is 7-(formyl diethyl acetal)-1,1,2,4,4-pentamethyl-tetralin.

12. The compound according to claim 9 which is 6-(acetyl diethyl ketal)-1,1,2,4,4,7-hexamethyl-tetralin.

13. The compound according to claim 9 which is 2,4,-dimethyl-2-(1,1,4,4-tetramethyl-tetralin-6-yl)-1,3-dioxolane.

14. The compound according to claim 9 which is 2-methyl-4-ethyl-2-(1,1,4,4-tetramethyl-tetralin-6-yl)-1,3-dioxolane.

15. The compound according to claim 9 which is 2,4-dimethyl-2-(1,1,2,4,4,7-hexamethyl-tetralin-6-yl)-1,3-dioxolane.

16. The compound according to claim 9 which is 2,4-dimethyl-2-(1,1,4,4-tetramethyl tetralin-6-y1)-1,3-dioxane.

17. An odorant composition comprising an olfactorily effective amount of a compound of the formula

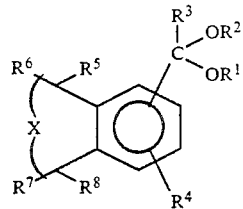

wherein:
$R^1$ and $R^2$ are selected from the group consisting of alkyl groups of one to four carbon atoms and alkenyl groups of two to four carbon atoms, or $R^1$ in combination with $R^2$ represents an alkylene group of two to four carbon atoms wherein the substituents on said alkylene group are selected from the group consisting of
(i) hydrogen,
(ii) an alkyl group having one to four carbon atoms,
(iii) an alkenyl group having two to four carbon atoms
(iv) an alkanol having one to four carbon atoms, and,
(v) an alkenol having one to four carbon atoms:
$R^3$ is selected from the group consisting of hydrogen and methyl;
$R^4$ is selected from the group consisting of hydrogen, methyl, ethyl, propyl and butyl;
$R^5$, $R^6$, $R^7$ and $R^8$ are selected from the group consisting of hydrogen methyl, ethyl normal-propyl and iso-propyl;
X is selected from the group consisting of

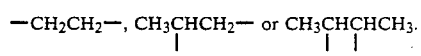

provided that
(i) the total number of carbon atoms in $R^1$ plus $R^2$ is not greater than six;
(ii) the total number of carbon atoms in the combination of groups $R^1$, $R^2$, $R^3$ and $R^4$ is not greater than eleven, and,
(iii) the total number of carbon atoms in the combination of groups $R^5$, $R^6$, $R^7$ and $R^8$ is not greater six.
and at least one other olfactory agent.

18. An odorant composition according to claim 17 wherein $R^1$ and $R^2$ are selected from the group consisting of alkyl groups of one to four carbon atoms and alkenyl groups of two to four carbon atoms and X is

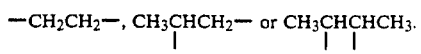

19. An odorant composition according to claim 17 wherein $R^1$ in combination with $R^2$ represents an alkylene group of two to four carbon atoms wherein the substituents on said alkylene group are selected from the group consisting of
(i) hydrogen,
(ii) an alkyl group having one to four carbon atoms,
(iii) an alkenyl group having two to four carbon atoms,
(iv) an alkanol having one to four carbon atoms, and, (v) an alkenol having one to four carbon atoms; and X is

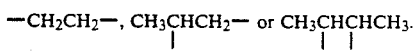

20. An odorant composition according to claim 17 wherein $R^1$ and $R^2$ are selected from the group consisting of alkyl groups of one to four carbon atoms and alkenyl groups of two to four carbon atoms and X is

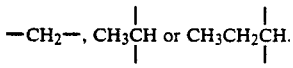

21. An odorant composition according to claim 17 wherein $R^1$ in combination with $R^2$ represents an alkylene group of two to four carbon atoms wherein the substituents on said alkylene group are selected from the group consisting of
(i) hydrogen,
(ii) an alkyl group having one to four carbon atoms,
(iii) an alkenyl group having two to four carbon atoms,
(iv) an alkanol having one to four carbon atoms, and,
(v) an alkenol having one to four carbon atoms; and X is

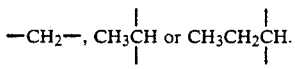

22. An odorant composition according to claim 17 having the structure

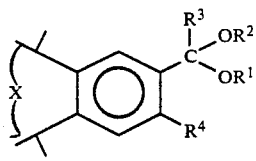

23. An odorant composition according to claim 22 wherein $R^4$ is hydrogen or methyl and X is

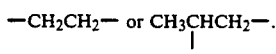

24. An odorant composition according to claim 22 wherein $R^4$ is hydrogen or methyl and X is

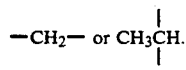

25. An odorant composition according to claim 23 wherein $R^1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

26. An odorant composition according to claim 24 wherein $R^1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

27. An odorant composition according to claim 25 wherein the compound is selected from the group consisting of 7-(formyl diethyl acetal)-1,1,2,4,4-pentamethyltetralin; 6-(acetyl diethyl ketal)-1,1,2,4,4,7-hexamethyl-tetralin; 2,4,-dimethyl-2-(1,1,4,4-tetramethyl-tetralin-6-yl)-1,3-dioxolane; 2-methyl-4-ethyl-2-(1,1,4,4-tetramethyl-tetralin-6-yl) -1,3-dioxolane; 2,4-dimethyl-2-(1,1,2,4,4,7-hexamethyl-tetralin-yl)-1,3-dioxolane; 2.4-dimethyl-2-(1,1,4,4-tetramethyl-tetralin-6-yl) -1,3-dioxolane.

28. A method for improving the odor of an odorant composition which comprises adding thereto an olfactorily effective amount of a compound of the formula

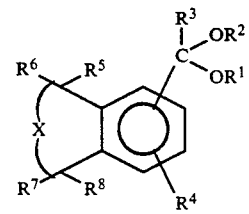

wherein:
$R^1$ and $R^2$ are selected from the group consisting of alkyl groups of one to four carbon atoms and alkenyl groups of two to four carbon atoms, or $R^1$ in combination with $R^2$ represents an alkylene group of two to four carbon atoms wherein the substituents on said alkylene group are selected from the group consisting of
(i) hydrogen.
(ii) an alkyl group having one to four carbon atoms,
(iii) an alkenyl group having two to four carbon atoms.
(iv) an alkanol having one to four carbon atoms, and,
(v) an alkenol having one to four carbon atoms;
$R^3$ is selected from the group consisting of hydrogen and methyl;
$R^4$ is selected from the group consisting of hydrogen, methyl, ethyl, propyl and butyl;
$R^5$, $R^6$, $R^7$ and $R^8$ are selected from the group consisting of hydrogen, methyl, ethyl, normal-propyl and iso-propyl; X is selected from the group consisting of

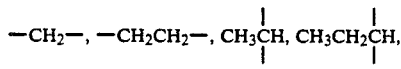

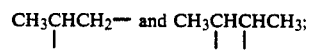

provided that
(i) the total number of carbon atoms in $R^1$ plus $R^2$ is not greater than six;
(ii) the total number of carbon atoms in the combination of groups $R^1$, $R^2$, $R^3$ and $R^4$ is not greater than eleven, and,
(iii) the total number of carbon atoms in the combination of groups $R^5$, $R^6$, $R^7$ and $R^8$ is not greater six.

29. A method according to claim 28 wherein $R^1$ and $R^2$ are selected from the group consisting of alkyl groups of one to four carbon atoms and alkenyl groups of two to four carbon atoms and X is

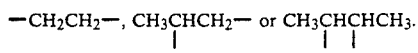

30. A method according to claim 28 wherein $R^1$ in combination with $R^2$ represents an alkylene group of two to four carbon atoms wherein the substituents on said alkylene group are selected from the group consisting of
  (i) hydrogen
  (ii) an alkyl group having one to four carbon atoms,
  (iii) an alkenyl group having two to four carbon atoms,
  (iv) an alkanol having one to four carbon atoms, and,
  (v) an alkenol having one to four carbon atoms; and X is

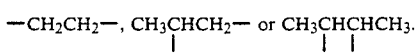

31. A method according to claim 28 wherein $R^1$ and $R^2$ are selected from from the group consisting of alkyl groups of one to four carbon atoms and alkenyl groups of two to four carbon atoms and X is

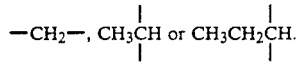

32. A method according to claim 28 wherein $R^1$ in combination with $R^2$ represents an alkylene group of two to four carbon atoms wherein the substituents on said alkylene group are selected from the group consisting of
  (i) hydrogen
  (ii) an alkyl group having one to four carbon atoms,
  (iii) an alkenyl group having two to four carbon atoms,
  (iv) an alkanol having one to four carbon atoms, and,
  (v) an alkenol having one to four carbon atoms;
and X is

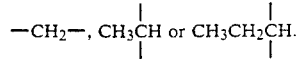

33. A method according to claim 28 having the structure

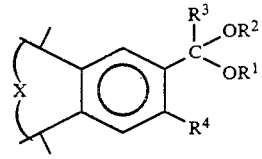

34. A method according to claim 33 wherein $R^4$ is hydrogen or methyl and X is

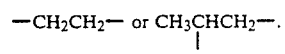

35. A method according to claim 33 wherein $R^1$ and $R^2$ or methyl and X is

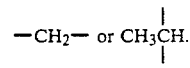

36. A method according to claim 34 wherein $R^1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

37. A method according to claim 35 wherein $R^1$ and $R^2$ are methyl or ethyl, or, $R^1$ in combination with $R^2$ represents an alkylene group of two or three carbon atoms wherein one of the substituents on said alkylene group is a methyl or ethyl group and the others are hydrogen.

38. A method according to claim 36 wherein the compound is selected from the group consisting of 7-(formyl diethyl acetal)-1,1,2,4,4-pentamethyl-tetralin; 6-(acetyl diethyl ketal)-1,1,2,4,4,7-hexamethyl-tetralin; 2,4,-dimethyl-2-(1,1,4,4-tetramethyl-tetralin-6-yl)-1,3-dioxolane; 2-methyl-4-ethyl-2-(1,1,4,4-tetramethyltetralin-6-yl)-1,3-dioxolane; 2,4-dimethyl-2-(1,1,2,4,4,7-hexamethyl-tetralin-6-yl)-1,3-dioxolane; 2,4-dimethyl-2-(1,1,4,4-tetramethyl-tetralin-6-yl)-1,3-dioxolane.

* * * * *